(12) United States Patent
Kostenich et al.

(10) Patent No.: US 11,911,138 B2
(45) Date of Patent: Feb. 27, 2024

(54) METHODS FOR IN VIVO FUNDUS MONOCHROMOTIC ANGIOGRAPHY IMAGING BLOOD-CONTAINING TISSUE BY UTILIZING TWO WAVELENGTH FROM 400NM TO 620 NM AND 620 NM TO 800 NM

(71) Applicants: Tel HaShomer Medical Research Infrastructure and Services Ltd., Ramat Gan (IL); RAMOT AT TEL AVIV UNIVERSITY LTD., Tel Aviv (IL)

(72) Inventors: Genady Kostenich, Tel Aviv (IL); Arie Orenstein, Tel Aviv (IL); Michael Belkin, Tel Aviv (IL)

(73) Assignees: Tel HaShomer Medical Research Infrastructure and Services Ltd., Ramat Gan (IL); Ramot At Tel AvivUniversity Ltd., Tel Aviv (IL)

( * ) Notice: Subject to any disclaimer, the term of this patent is extended or adjusted under 35 U.S.C. 154(b) by 1101 days.

(21) Appl. No.: 16/272,616

(22) Filed: Feb. 11, 2019

(65) Prior Publication Data

US 2019/0183360 A1 Jun. 20, 2019

Related U.S. Application Data

(63) Continuation of application No. 13/984,303, filed as application No. PCT/IB2012/050563 on Feb. 8, 2012, now abandoned.

(30) Foreign Application Priority Data

Feb. 9, 2011 (GB) ...................................... 1102209

(51) Int. Cl.
*A61B 5/026* (2006.01)
*A61B 1/04* (2006.01)
(Continued)

(52) U.S. Cl.
CPC ............ *A61B 5/0261* (2013.01); *A61B 1/041* (2013.01); *A61B 3/12* (2013.01); *A61B 3/1241* (2013.01);
(Continued)

(58) Field of Classification Search
CPC ......... A61B 5/0261; A61B 1/041; A61B 3/12; A61B 3/1241; A61B 5/0075; A61B 5/489;
(Continued)

(56) References Cited

U.S. PATENT DOCUMENTS 4,579,430 A 4/1986 Bille
5,141,303 A 8/1992 Yamamoto et al.
(Continued)

FOREIGN PATENT DOCUMENTS

EP 2328339 A2 6/2011
GB 2487940 A 8/2012
(Continued)

OTHER PUBLICATIONS

Fisher et al.(Hypermedia Image Processing Reference, 1996, Published by J. Wiley & Sons). (Year: 1996).*
(Continued)

*Primary Examiner* — Serkan Akar
(74) *Attorney, Agent, or Firm* — Dorsey & Whitney LLP

(57) ABSTRACT

Disclosed are methods and devices useful for imaging blood-containing tissue, for example for angiography, especially retinal angiography, whereby an image is generated by dividing pixels of an image acquired at some wavelength range by corresponding pixels of an image acquired at a different wavelength range. In some embodiments, a first wavelength range includes predominantly light having wavelengths between about 400 nm and about 620 nm and a second wavelength range includes predominantly light
(Continued)

having wavelengths between about 620 nm and about 800 nm.

12 Claims, 7 Drawing Sheets

(51) Int. Cl.
*A61B 3/12* (2006.01)
*A61B 5/00* (2006.01)

(52) U.S. Cl.
CPC ............ *A61B 5/0075* (2013.01); *A61B 5/489* (2013.01); *A61B 5/0077* (2013.01); *A61B 5/0084* (2013.01); *F04C 2270/041* (2013.01)

(58) Field of Classification Search
CPC ................. A61B 5/0077; A61B 5/0084; F04C 2270/041; G06T 5/50; G06T 7/0012
See application file for complete search history.

(56) References Cited

U.S. PATENT DOCUMENTS

| | | | |
|---|---|---|---|
| 5,722,407 A | 3/1998 | Klingenbeck-regn et al. | |
| 6,083,158 A | 7/2000 | Bearman et al. | |
| 6,091,984 A | 7/2000 | Perelman et al. | |
| 6,104,939 A | 8/2000 | Groner et al. | |
| 6,276,798 B1 | 8/2001 | Gil et al. | |
| 6,556,853 B1 | 4/2003 | Cabib et al. | |
| 6,790,174 B2 | 9/2004 | Kaneko et al. | |
| 6,912,412 B2 | 6/2005 | Georgakoudi et al. | |
| 7,282,723 B2 | 10/2007 | Schomacker et al. | |
| 8,649,849 B2 | 2/2014 | Liu et al. | |
| 2001/0007920 A1 | 7/2001 | Hayashi | |
| 2002/0062061 A1 | 5/2002 | Kaneko et al. | |
| 2006/0235308 A1 | 10/2006 | Van Beek et al. | |
| 2006/0276698 A1 | 12/2006 | Halldorsson et al. | |
| 2007/0146632 A1 | 6/2007 | Chipman | |
| 2007/0219439 A1 | 9/2007 | Vilser et al. | |
| 2007/0253033 A1 | 11/2007 | Johansen et al. | |
| 2009/0076396 A1 | 3/2009 | Yaroslavsky et al. | |
| 2009/0204009 A1 | 8/2009 | Powers et al. | |
| 2009/0216085 A1 | 8/2009 | Yamazaki | |
| 2009/0244339 A1 | 10/2009 | Murooka et al. | |
| 2009/0270702 A1 | 10/2009 | Zeng et al. | |
| 2010/0106025 A1 | 4/2010 | Sarfaty et al. | |
| 2012/0252057 A1 | 10/2012 | Schrelber et al. | |
| 2012/0259229 A1 | 10/2012 | Wang et al. | |
| 2012/0277559 A1* | 11/2012 | Kohl-Bareis | A61B 5/0261 600/479 |
| 2015/0173623 A1 | 6/2015 | Kostenich et al. | |
| 2015/0182169 A1 | 7/2015 | Kostenich et al. | |

FOREIGN PATENT DOCUMENTS

| | | |
|---|---|---|
| JP | S59115024 A | 7/1984 |
| JP | H02295539 A | 12/1990 |
| JP | 03080834 | 4/1991 |
| JP | 200041942 | 2/2000 |
| JP | 200234893 A | 2/2002 |
| JP | 2003102680 A | 4/2003 |
| JP | 2003334162 A | 11/2003 |
| JP | 2005124823 A | 5/2005 |
| JP | 2006116153 A | 5/2006 |
| JP | 2006166990 A | 6/2006 |
| JP | 2007501646 A | 2/2007 |
| JP | 2007125403 A | 5/2007 |
| JP | 2007530186 A | 11/2007 |
| JP | 2008086605 A | 4/2008 |
| JP | 2009153621 A | 7/2009 |
| JP | 2009201685 A | 9/2009 |
| JP | 2009246840 A | 10/2009 |
| JP | 2012107942 A | 6/2012 |
| WO | 2005110186 A2 | 11/2005 |

OTHER PUBLICATIONS

International Search Report and Written Opinion from International Application No. PCT/IB2012/050563 dated May 30, 2012.

* cited by examiner

METHODS FOR IN VIVO FUNDUS MONOCHROMOTIC ANGIOGRAPHY IMAGING BLOOD-CONTAINING TISSUE BY UTILIZING TWO WAVELENGTH FROM 400NM TO 620 NM AND 620 NM TO 800 NM

CROSS-REFERENCE TO RELATED APPLICATIONS

The present application is a continuation of U.S. application Ser. No. 13/984,303 filed on 6 Mar. 2014, which is a U.S. national stage application of PCT International Application No. PCT/IB2012/050563 filed on 8 Feb. 2012, which claims priority to United Kingdom Patent Application No. 1102209.2 filed 9 Feb. 2011, the disclosure of each of which is incorporated herein, in its entirety, by this reference.

FIELD AND BACKGROUND OF THE INVENTION

The invention, in some embodiments, relates to the field of medical imaging, and more particularly but not exclusively, to methods and devices suitable for imaging blood-containing tissue, for example for angiography, especially retinal angiography.

Angiography is a technique for the in vivo imaging of blood vessels.

In some instances, angiography is performed by administering a radio-opaque contrast agent in the blood vessels of a living subject and then acquiring an image of the blood vessels using an X-ray imaging modality. Such methods are useful, for example, to acquire a 3-dimensional representation of cerebral blood vessels.

To avoid the use of an X-ray imaging modality, it is known to acquire a visible light image of shallow blood vessels in a bodily surface, for example, in the retina or mucosa such as the gastrointestinal luminal walls, with the use of fluorescence angiography. A fluorescent agent (e.g., sodium fluorescein or indocyanine green) is administered into the blood vessels of a subject. The surface to be imaged is illuminated with a fluorescence-exciting wavelength (e.g., 490 nm for sodium fluorescein, 800 nm for indocyanine green) and a camera used to acquire an image from the light emitted by the fluorescent agent (e.g., 530 nm for sodium fluorescein, 830 nm for indocyanine green).

It is also known to perform optical angiography, the use a suitable camera to acquire a visible-light color image of blood vessels, thus avoiding the complexity, time and potential health hazards associated with the administration of a fluorescent agent.

Visible-light color images often have insufficient contrast to clearly discern smaller blood vessels. It has been found that "red-free" images (e.g., images acquired where the camera lens is functionally associated with a green filter to prevent red light from being gathered) have greater contrast than color images.

In many fields, for example in the field of retinal angiography, it would be useful to have improved performance for example, increased contrast and/or greater spatial resolution. Such improved performance may allow gathering information useful in screening or diagnosing conditions such as cancer-related angiogenesis, diabetic retinopathy, age-relate macular degeneration and cardiovascular and brain diseases that have been shown to be related to the morphology of the retinal microvasculature.

Some may consider U.S. Pat. Nos. 6,083,158; 6,104,939; 6,276,798; 6,556,853 as well as U.S. Patent Application Publication No. 2007/0253033 and as providing background to some embodiments of the teachings herein.

SUMMARY OF THE INVENTION

Some embodiments of the invention relate to methods and devices suitable for imaging blood-containing tissue, for example for performing angiography, that in some embodiments have advantages over known imaging methods and devices.

Some embodiments of the methods and devices described herein an image 1s generated by dividing pixels of an image acquired at some wavelength range by corresponding pixels of an image acquired at a different wavelength range. In some embodiments, a first wavelength range includes predominantly light having wavelengths between about 400 nm and about 620 nm and a second wavelength range includes predominantly light having wavelengths between about 620 nm and about 800 nm.

According to an aspect of some embodiments of the invention, there is provided a method of generating an image of the surface of biological tissue, comprising:

a) acquiring a first pixelated image of an area of interest of the surface at a first wavelength range of light, the first wavelength range including predominantly light having wavelengths of between about 400 nm and about 620 nm;

b) acquiring a second pixelated image of the area of interest of the surface at a second wavelength range of light, the second wavelength range including predominantly light having wavelengths of between about 620 nm and about 800 nm;

c) generating a monochromatic third pixelated image from the first image and the second image by:

for each desired location i of the area of interest, identifying a corresponding pixel P1($i$) in the first image and a corresponding pixel P2($i$) in the second image; and calculating a pixel P3($i$) in the third image corresponding to the location i, by dividing one of P1($i$) and P2($i$) by the other.

According to an aspect of some embodiments of the invention, there is also provided a device useful for generating an image of the surface of biological tissue, comprising:

a) an image-acquirer suitable for acquiring a first pixelated image of an area of interest of the surface of biological tissue with a first wavelength range of light, the first wavelength range including predominantly light having wavelengths of between about 400 nm and about 620 nm;

b) an image-acquirer suitable for acquiring a second pixelated image of the area of interest with a second wavelength range of light, the second wavelength range including predominantly light having wavelengths of between about 620 nm and about 800 nm; and c) a processor configured to generate a monochromatic third pixelated image from the first image and the second image by:

for each desired location i of an area of interest, identifying a corresponding pixel P1($i$) in the first image and a corresponding pixel P2($i$) in the second image; and calculating a pixel P3($i$) in the third image corresponding to the location i, by dividing one of P1($i$) and P2($i$) by the other.

As used herein, for clarity the term "image" refers to a visible image (e.g., as displayed on permanent media such as on printed paper or electronic media such as a display screen (LED, LCD, CRT)), as well as data (especially electronic data) representing the image including data stored, for example, on magnetic or electrical media (e.g., flash memory, magnetic disk, magnetic tape).

As used herein, for clarity the term "pixel" refers to an element making up a pixelated image (displayed or stored as data) and also to the value of the pixel, as the context dictates.

Unless otherwise defined, all technical and scientific terms used herein have the same meaning as commonly understood by one of ordinary skill in the art to which the invention pertains. In case of conflict, the specification, including definitions, will control.

As used herein, the terms "comprising", "including", "having" and grammatical variants thereof are to be taken as specifying the stated features, integers, steps or components but do not preclude the addition of one or more additional features, integers, steps, components or groups thereof.

As used herein, the indefinite articles "a" and "an" mean "at least one" or "one or more" unless the context clearly dictates otherwise.

Embodiments of methods and/or devices described herein may involve performing or completing selected tasks manually, automatically, or a combination thereof. Some methods and/or devices described herein are implemented with the use of components that comprise hardware, software, firmware or combinations thereof. In some embodiments, some components are general-purpose components such as general purpose computers, digital processors or oscilloscopes. In some embodiments, some components are dedicated or custom components such as circuits, integrated circuits or software.

For example, in some embodiments, some of an embodiment is implemented as a plurality of software instructions executed by a data processor, for example which is part of a general-purpose or custom computer. In some embodiments, the data processor or computer comprises volatile memory for storing instructions and/or data and/or a non-volatile storage, for example, a magnetic hard-disk and/or removable media, for storing instructions and/or data. In some embodiments, implementation includes a network connection. In some embodiments, implementation includes a user interface, generally comprising one or more of input devices (e.g., allowing input of commands and/or parameters) and output devices (e.g., allowing reporting parameters of operation and results.

BRIEF DESCRIPTION OF THE FIGURES

Some embodiments of the invention are herein described with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures.

DESCRIPTION OF SOME EMBODIMENTS OF THE INVENTION

Figure 1A:
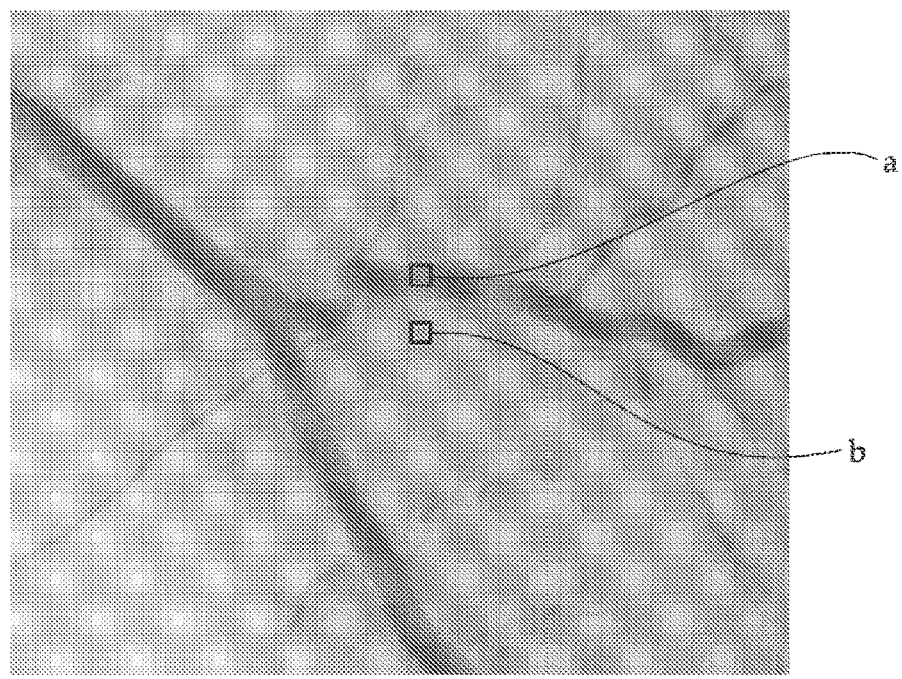
FIG. 1A is a reproduction of an image of the surface of the inner side of a flap of abdominal skin of a mouse, with two regions marked: a region including a blood vessel (a) and a region devoid of blood vessels (b)
Figure 1B:
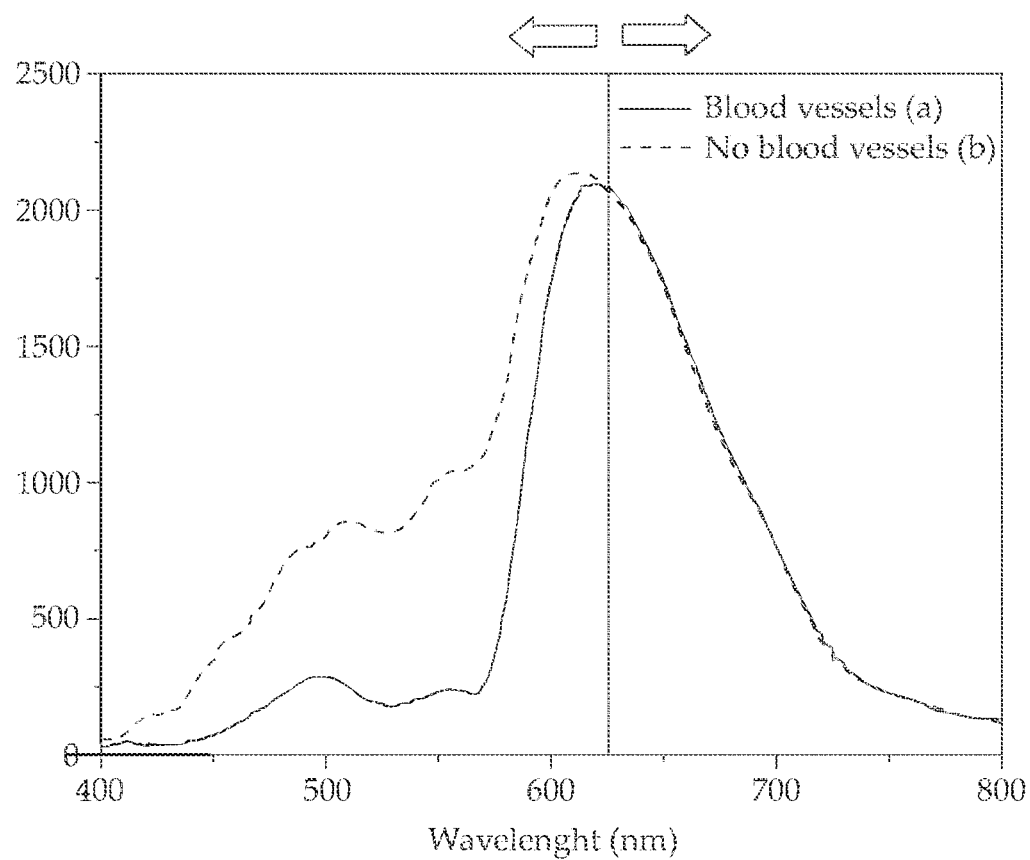
FIG. 1B are the reflectance spectra of regions a and b in Figure IA between 400 nm and 800 nm.

Some embodiments of the invention relate to methods and devices useful for imaging blood-containing tissue, for example for angiography, especially retinal angiography. In some embodiments, an image is generated by dividing pixels of an image acquired at some wavelength range by corresponding pixels of an image acquired at a different wavelength range. In some embodiments, a first wavelength range includes predominantly light having wavelengths between about 400 nm and about 620 nm and a second wavelength range includes predominantly light having wavelengths between about 620 nm and about 800 nm.

The principles, uses and implementations of the teachings of the invention may be better understood with reference to the accompanying description and figures. Upon perusal of the description and figures present herein, one skilled in the art is able to implement the teachings of the invention without undue effort or experimentation. In the figures, like reference numerals refer to like parts throughout.

Before explaining at least one embodiment of the invention in detail, it is to be understood that the invention is not necessarily limited in its application to the details of construction and the arrangement of the components and/or methods set forth herein. The invention is capable of other embodiments or of being practiced or carried out in various ways. The phraseology and terminology employed herein are for descriptive purpose and should not be regarded as limiting.

Known methods for acquiring images of blood-containing tissue, such as in the field of angiography, have various shortcomings. Some methods require administration of compositions into the body, for example fluorescein or indocyanine compositions. Images acquired using known methods that do not include administration of such compositions are often insufficiently clear.

In Figure IA an image of the surface of the inner side of a flap of abdominal skin of a mouse is reproduced with two regions marked: a region including a blood vessel (a) and a region devoid of blood vessels (b).

In Figure IB are depicted the reflectance spectra of region a (blood vessel) and b (no blood vessel) between 400 nm and 800 nm as acquired by the Inventor using a spectral imaging camera. It is seen that between 620 nm and 800 nm, the reflectance of blood-containing tissue (a) and tissue substantially devoid of blood (b) is substantially the same. It is also seen that between 400 nm and 620 nm, the reflectance of blood-containing tissue (a) is significantly lower than that of the tissue substantially devoid of blood (b), attributable to the absorption of light having such wavelengths by blood.

Herein are disclosed methods and devices useful for imaging blood-containing tissue, for example for angiography, especially retinal angiography. In some embodiments, an image is generated by dividing pixels of one image by corresponding pixels of another image, a first image acquired at a first wavelength range including predominantly light having higher absorbance in blood than non-blood bodily tissue, generally having wavelengths of between about 400 nm and about 620 nm and a second image acquired at a second wavelength range including predominantly light having absorbance in blood similar to that of non-blood tissue generally having wavelengths of between about 620 nm and about 800 nm. It has been surprisingly found that in some embodiments, such a generated image has greater apparent detail due to higher contrast and/or greater spatial detail when compared to images acquired using known methods.

Figure 2A:
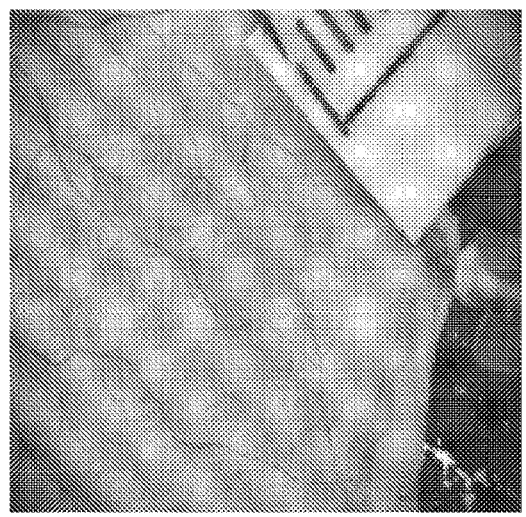
FIG. 2A is a black-and-white reproduction of a standard RGB image of the surface of the inner side of a flap of abdominal skin of a mouse.
Figure 2B:
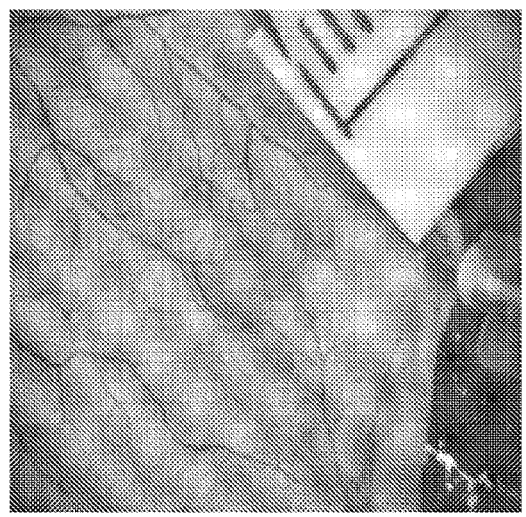
FIG. 2B is a reproduction of a standard monochrome red-free narrow band (520 nm-580 nm) image of the surface of the inner side of a flap of abdominal skin of a mouse.
Figure 2C:
FIG. 2C is a reproduction of an image of the surface of the inner side of a flap of abdominal skin of a mouse generated in accordance with an embodiment of the method as described herein, where the first wavelength range was 400 nm to 600 nm and the second wavelength range was 600 nm to 800 nm.

In FIGS. 2, three different pixelated images of the same surface of the inner side of a flap of abdominal skin of a mouse acquired and generated by the Inventors using a spectral camera are depicted:

in FIG. 2A, a standard RGB image of the surface is reproduced in black and white;

in FIG. 2B, a standard monochrome red-free narrow band (520 nm-580 nm) image of the surface is reproduced; and in FIG. 2C, an image generated in accordance with an embodiment of the method described herein (see Examples section) is reproduced where the first wavelength range was 400 nm to 600 nm and the second wavelength range was 620 nm to 800 nm.

Despite the relatively low quality of the reproductions in FIGS. 2A, 2B and 2C, it is seen that the teachings herein provide an image with greater apparent detail.

It is seen that the image in FIG. 2C generated in accordance with the teachings herein has an unexpectedly superior contrast to the images in FIGS. 2A and 2B.

It is also seen that the image in FIG. 2C generated in accordance with the teachings herein has an unexpectedly superior spatial resolution to the images in FIGS. 2A and 2B. Although not wishing to be held to any one theory, it is currently believed that in the known methods, the spatial resolution of the images is limited by the presence of photons at specific wavelengths back-scattered by the tissue including tubular walls of the blood vessels in the tissue. Apparently, the teachings herein reduce the effect of such back-scattered photons so that the edges of the blood vessels in an image generated in accordance with the teachings herein are more clearly defined.

Whatever the reasons, the teachings herein have exceptional utility, allowing acquisition of high contrast and/or detailed images, in some embodiments in real time, of capillaries, arteries, veins, hemorrhages and some blood-rich tumors. Images having greater spatial resolution and/or greater contrast make automated diagnosis methods (e.g., methods using image processing or image-comparison techniques) more accurate. Images having greater spatial resolution and/or greater contrast provide a health-care professional with more accurate information to diagnose some pathologies such as bleeding, cancer-related angiogenesis (e.g., retinal tumors such as melanoma), diabetic retinopathy, age-related macular degeneration and cardiovascular and brain diseases.

Method for Generating an Image

According to an aspect of some embodiments of the teachings herein, there is provided a method suitable for generating an image of the surface of biological tissue comprising:

a) acquiring a first pixelated image of an area of interest of the surface at a first wavelength range of light, the first wavelength range including predominantly light having wavelengths of between about 400 nm and about 620 nm;

b) acquiring a second pixelated image of the area of interest of the surface at a second wavelength range of light, the second wavelength range including predominantly light having wavelengths of between about 620 nm and about 800 nm;

c) generating a monochromatic third pixelated image from the first image and the second image by:

for each desired location i of an area of interest, identifying a corresponding pixel $P1(i)$ in the first image and a corresponding pixel $P2(i)$ in the second image; and calculating a pixel $P3(i)$ in the third image corresponding to the location i, by dividing one of $P1(i)$ and $P2(i)$ by the other.

The biological surface is any suitable biological surface. In some embodiments, the biological surface is a biological surface selected from the group consisting of a retina, skin, mucosa, gastrointestinal mucosa, oral mucosa, a gynecological tract surface, and a respiratory tract surface.

In some embodiments, the first image is a monochromatic image. In some embodiments, the second image is a monochromatic image.

In some embodiments, the third image has increased contrast between blood-containing features (such as blood vessels) and adjacent tissue, relative to comparable color or red-free images.

In some embodiments, the third image has increased spatial resolution at the border between blood-containing features (such as blood vessels) and adjacent tissue, relative to comparable color or red-free images.

Typically but not necessarily, the first, second and third images all are of the same size (in terms of pixels) and are of the same area of interest of the surface. Consequently, during the generating of the third image, all pairs of corresponding pixels from the first and second image are used together to calculate a corresponding pixel of the third image.

In some embodiments, the first and second image are of the same size (in terms of pixels) and are of the same area of interest of the surface but the third image is smaller (e.g., of the same area of interest but fewer pixels to have lower resolution, or of a smaller area of interest having the same or lower resolution). In such embodiments, the pixels constituting the third image are calculated from the corresponding pairs of pixels from the first and second image.

In some embodiments, one of the first and second image is smaller than the other (in terms of pixels) and/or in terms of the area of interest of the surface. In some such embodiments, the third image is of the same size as the smaller of the first and second images. In some such embodiments, the third image is smaller and/or of a smaller area of interest. In such embodiments, the pixels constituting the third image are calculated from the corresponding pairs of pixels from the first and second image.

In some embodiments, the method further comprises storing the third image, for example on a flash memory (e.g., SD card) or magnetic memory (e.g., hard disk) data storage component. In some embodiments, the method further comprises displaying the third image in a manner visible to a person, for example on a display screen (e.g., LED, LCD or CRT display screen) or on permanent media (printed on paper of film). In some embodiments, the displaying is in real time.

In some embodiments, the third image undergoes post-processing prior to storing and/or displaying. Typical post-processing includes, but is not limited to, cropping, rotation, resizing and changes in color depth.

In some embodiments, prior to the generating of the third image, the pixels of the first image, of the second image or of both the first and the second image are normalized relative to some specific wavelength, for example for intensity balancing.

In some embodiments, a mathematical formula describing the calculating of a pixel of the third image from the two corresponding pixels of the first and second images is substantially a mathematical formula selected from the group consisting of:

$P3(i)=[(xP1(i)+m)^A/(yP2(i)+n)^B]$ and $P3(i)=[(yP2(i)+n)^B/(xP1(i)+m)^A]$, wherein A and B are, independently, any suitable (preferably real) positive number except 0 and including 1; and wherein x and y are, independently, any suitable (preferably real) number including 1; and wherein m and n are, independently, any suitable (preferably real) number including 0.

In some embodiments, the mathematical formula is substantially a mathematical formula selected from the group consisting of $P3(i)=[P1(i)/P2(i)]$ and $P3(i)=[(P2(i)/P1(i)]$.

In some embodiments, the method further comprises illuminating the area of interest with light comprising wavelengths within the first wavelength range during the acquiring of the first pixelated image; and illuminating the area of interest with light comprising wavelengths within the second wavelength range during the acquiring of the second pixelated image. In some embodiments, the illuminating is with incoherent light. In some embodiments, the illuminating is with polarized light. In some embodiments, the illuminating with light comprising wavelengths within the first wavelength range is simultaneous with the illuminating with light comprising wavelengths within the second wavelength range. In some such embodiments, the illuminating is with white light (e.g., a light-emitting diode emitting white light, a white-light lamp). In some such embodiments, the illuminating is with light having at least two discrete wavelengths of light: at least one discrete wavelength within the first wavelength range (e.g., with a light-emitting diode emitting yellow, green or blue light) and at least one discrete wavelength within the second wavelength range (e.g., with a light-emitting diode emitting red light).

In some embodiments, the acquiring of the first pixelated image is not simultaneous with the acquiring of the second pixelated image, and the method further comprises:
illuminating the area of interest with light comprising wavelengths within the first wavelength range (e.g., with a light-emitting diode emitting yellow, green or blue light) during the acquiring of the first pixelated image; and
illuminating the area of interest with light comprising wavelengths within the second wavelength range (e.g., with a light-emitting diode emitting red light) during the acquiring of the second pixelated image.

In some such embodiments, during the acquiring of the first pixelated image, illuminating the area of interest is with light substantially devoid of wavelengths within the second wavelength range. In some such embodiments, during the acquiring of the second pixelated image, illuminating the area of interest is with light substantially devoid of wavelengths within the first wavelength range.

Generally, the first image and the second image are acquired using one or more pixelated image-acquirers as known in the field of digital photography, e.g., CCD arrays and CMOS arrays that typically use one or more arrays of light-sensitive sensors to acquire an image from light gathered by an objective.

In some embodiments, the first image and the second image are acquired substantially simultaneously.

For example, in some such embodiments the method comprises:
directing light collected for acquiring the first image from the area of interest to a first image-acquirer to acquire the first image; and
directing light collected for acquiring the second image from the area of interest to a second image-acquirer different from the first image-acquirer to acquire the second image.

In some embodiments, such directing of light is achieved using optical elements such as one or more of light filters, polarization filters, beam splitters, dichroic and trichroic prisms that direct the different wavelengths of light to the different image-acquirers.

For example, in some such embodiments the method comprises:
directing light collected for acquiring the first image and the second image from the area of interest to a single image-acquirer;
separating data acquired by the single image-acquirer constituting the first image from data acquired by the single image-acquirer constituting the second image.

In some embodiments, such separating of data is performed by using different color outputs of a single-image-acquirer to generate the first and the second image. For example, in some such embodiments, an image-acquirer is a Foveon-X3 CMOS image-acquirer (National Semiconductor, Santa Clara, Calif., USA) that has separate outputs for blue, green and red pixels. For example, in some such embodiments, an image-acquirer is a CCD or CMOS image-acquirer including a Bayer or other wavelength filter that has separate outputs for red, green and blue pixels (RGB), or other wavelength filters such as red, green, blue, emerald pixels (RGBE filter), red, green, blue and white pixels (RGBW) and cyan, magenta, yellow and white pixels (CMYW).

In some embodiments, cross-polarization filters are used for illumination light and for collected light, which in some embodiments reduces or eliminates some of the negative effects of specular reflections.

In some embodiments, the first and second image are acquired sequentially. To overcome the possibility that the area of interest moved in the frame of the images between acquisition of the first and second images, stitching algorithms (such as known in the field of digital photography) are typically used to match a pixel from the first image and a corresponding pixel from the second image to calculate a corresponding pixel of the third image.

In some such embodiments, a device includes a single multicolor image-acquirer. In some such embodiments, a device includes a single monochrome image-acquirer.

For example, in some such embodiments, the image-acquirer is functionally associated with a changing (e.g., rotating) wavelength filter that changes from a first state (that allows light from the first wavelength range to reach the image-acquirer) to a second state (that allows light from the second wavelength range to reach the image-acquirer). When the wavelength filter is in a first state, predominantly (in some embodiments only) light from the first wavelength range of light reaches the image-acquirer and the first image is acquired.

When the wavelength filter is in a second state, predominantly (in some embodiments, only) light from the second wavelength range of light reaches the image-acquirer and the second image is acquired.

For example, in some such embodiments, the area of interest is alternately illuminated with light having different wavelengths. When the area of interest is illuminated predominantly with light having the first wavelength range of light, the first image is acquired. When the area of interest is illuminated predominantly with light having the second wavelength range the second image is acquired.

In any given embodiment, the first image is acquired at a first wavelength range of light, that predominantly includes light having wavelengths of between about 400 nm and about 620 nm and the second image is acquired at a second wavelength range of light, that predominantly includes light having wavelengths of between about 620 nm and about 800.

In some embodiments, the first image is acquired at a first wavelength range of light, that exclusively includes light having wavelengths of between about 400 nm and about 620 nm: it is currently believed that in some instances such embodiments provide the greatest improvement in image-quality.

That said, in some embodiments the first image is acquired with some light having wavelengths of between about 620 nm and about 800. In such embodiments, the first wavelength range and the second wavelength range are together chosen to achieve the desired improvement in image-quality.

In some embodiments, the second image is acquired at a second wavelength range of light, that exclusively includes light having wavelengths of between about 620 nm and about 800 nm: it is currently believed that in some instances such embodiments provide the greatest improvement in image-quality.

That said, in some embodiments the second image is acquired with some light having wavelengths of between about 400 nm and about 620. For example, the second image used in generating the image reproduced in FIG. 2C included light having wavelengths of about 600 nm and 800 nm. In such embodiments, the first wavelength range and the second wavelength range are together chosen to achieve the desired improvement in image quality.

For example, in some embodiments, the first image is acquired at a first wavelength range of light, that exclusively includes light having wavelengths of between about 400 nm and about 620 nm (e.g., all light having a wavelength from 400 nm to 620 nm, or light having a wavelength from about 400 nm to about 600 nm) and the second image is acquired at a second wavelength range of light, that includes light having wavelengths of between about 400 nm and about 800 nm.

In some embodiments, the first wavelength range is centered between a lower wavelength of about 400 nm (in some embodiments, between about 400 nm and about 450 nm) and an upper wavelength of about 620 nm (in some embodiments between about 550 nm and about 620 nm). In some embodiments, the first wavelength range is centered between a lower wavelength of about 450 nm and an upper wavelength of about 580 nm. In some embodiments, the first wavelength range is centered between a lower wavelength of about 480 nm and an upper wavelength of about 550 nm.

In some embodiments, the first wavelength range has a narrow bandwidth: e.g., having a bandwidth of less than about 5 nm, less than about 3 nm and even less than about 2 nm.

In some embodiments, the first wavelength range has a wide bandwidth, allowing more light to be gathered to acquire the first image with the concomitant high signal to noise ratio. In some such embodiments, the first wavelength range has a bandwidth of at least about 5 nm, at least about 10 nm, at least about 20 nm, at least about 40 nm and even at least about 80 nm.

In some embodiments, the first wavelength range is centered between a lower wavelength of about 620 nm (in some embodiments, between about 620 nm and about 650 nm) and an upper wavelength of about 800 nm (in some embodiments between about 700 nm and about 800 nm). In some embodiments, the second wavelength range is centered between a lower wavelength of about 620 nm and an upper wavelength of about 700 nm. In some embodiments, the second wavelength range is centered between a lower wavelength of about 620 nm and an upper wavelength of about 650 nm.

In some embodiments, the second wavelength range has a narrow bandwidth: e.g., having a bandwidth of less than about 5 nm, less than about 3 nm and even less than about 2 nm.

In some embodiments, the second wavelength range has a wide bandwidth, allowing more light to be gathered to acquire the second image with the concomitant high signal to noise ratio. In some such embodiments, the second wavelength range has a bandwidth of at least about 5 nm, at least about 10 nm, at least about 20 nm, at least about 40 nm and even at least about 80 nm.

Embodiments of the method may be implemented using any suitable device. For example, the first and second pixelated images may be acquired using a standard camera (with required modification). That said, in some embodiments it is preferable to use a device as described herein.

Device for Generating an Image

According to an aspect of some embodiments of the teachings herein, there is provided a device suitable for generating an image of the surface of biological tissue comprising:

a) an image-acquirer suitable for acquiring a first pixelated image of an area of interest of the surface of biological tissue with a first wavelength range of light, the first wavelength range including predominantly light having wavelengths of between about 400 nm and about 620 nm;

b) an image-acquirer suitable for acquiring a second pixelated image of the area of interest of the surface of biological tissue with a second wavelength range of light, the second wavelength range including predominantly light having wavelengths of between about 620 nm and about 800 nm;

c) a processor configured to generate (in some embodiments, automatically) a monochromatic third pixelated image from the first image and the second image by:

for each desired location i of an area of interest, identifying a corresponding pixel $P1(i)$ in the first image and a corresponding pixel $P2(i)$ in the second image; and calculating a pixel $P3(i)$ in the third image corresponding to the location i, by dividing one of $P1(i)$ and $P2(i)$ by the other.

The device is any suitable device. In some embodiments, the device is a device selected from the group consisting of a medical camera, an ingestible endoscope, an endoscope, an ophthalmoscope and a fundus camera.

The first wavelength range is any suitable wavelength range, as described above. The second wavelength range is any suitable wavelength range, as described above.

The calculating is performed substantially as described above.

In some embodiments, the device further comprises an illuminator configured: to illuminate an area of interest with light comprising wavelengths within the first wavelength range during acquisition of a first pixelated image; and to illuminate an area of interest with light comprising wavelengths within the second wavelength range during acquisition of a second pixelated image. In some embodiments, the illumination light is incoherent light. In some embodiments, the illumination light is polarized light.

In some embodiments, the illuminator is configured to simultaneously illuminate an area of interest with light comprising wavelengths within the first wavelength range and wavelengths within the second wavelength range. In some such embodiments, the illuminator includes a source of white light. In some such embodiments, the illuminator includes a source of at least two discrete wavelengths of light, at least one discrete wavelength of light within the first wavelength range and at least one discrete wavelength of light within the second wavelength range.

In some embodiments, the illuminator includes a source of at least two discrete wavelengths of light, at least one discrete wavelength of light within the first wavelength range and at least one discrete wavelength of light within the second wavelength range, and the device is configured:

to illuminate an area of interest with a discrete wavelength of light within the first wavelength range only during acquisition of first pixelated image; and to illuminate an area of interest with a discrete wavelength of light within the second wavelength range only during acquisition of second pixelated image.

In some embodiments, the image-acquirer suitable for acquiring the first pixelated image and the image-acquirer suitable for acquiring the second pixelated image are the same image-acquirer, generally a multicolor image-acquirer.

In some embodiments, the image-acquirer suitable for acquiring the first pixelated image and the image-acquirer suitable for acquiring the second pixelated image are different image-acquirers, in some embodiments monochrome image-acquirers and in some embodiments multicolor image-acquirers. In some embodiments, the device further comprises at least one optical element to direct light of the first wavelength range to the first-image acquirer and light of the second wavelength range to the second-image acquirer.

In some embodiments, the device is configured to acquire the first image and the second image substantially simultaneously.

In some such embodiments, the device comprises an optical element that directs light gathered by an objective to different image-acquirers (monochrome or multicolor), at least one image-acquirer configured to acquire the first image and at least one image-acquirer configured to acquire the second image. In some such embodiments, the optical element is, for example, a dichroic prism or a trichroic prism that directs light from the first wavelength range to the first-image acquirer or acquirers and directs light from the second wavelength range to the second-image acquirer or acquirers. In some such embodiments, the optical element is, for example, a beam splitter, that directs some light to the first-image acquirer or acquirers through a wavelength filter that allows only light of the first wavelength range to pass and directs some light to the second-image acquirer or acquirers through a wavelength filter that allows only light of the second wavelength range to pass.

In some such embodiments, the device comprises a single multicolor image-acquirer configured to acquire both the first and the second image, In some such embodiments, the multicolor image-acquirer has separate outputs for each color, for example a Foveon-X3 CMOS image-acquirer that has separate outputs for blue, green and red pixels or a CCD or CMOS image-acquirer including a Bayer or other wavelength filter that has separate outputs for red, green and blue pixels (RGB), or other wavelength filters such as red, green, blue, emerald pixels (RGBE filter).

In some embodiments, the device is configured to acquire the first image and the second image sequentially. In some such embodiments, the device comprises a single image-acquirer, in some embodiments a multicolor image-acquirer, in some embodiments a monochrome image-acquirer. In some embodiments, the image-acquirer is functionally associated with a changing (e.g., rotating) wavelength filter that changes from a first state (that allows light from the first wavelength range to reach the image-acquirer) to a second state (that allows light from the second wavelength range to reach the image-acquirer). When the wavelength filter is in a first state, the device is configured to acquire a first image as only light from the first wavelength range of light reaches the image-acquirer and the first image is acquired. When the wavelength filter is in a second position, the device is configured to acquire a second image as only light from the second wavelength range of light reaches the image-acquirer and the second image is acquired.

In some embodiments, the device includes an illuminator configured to alternately illuminate an area of interest with light having different wavelengths. The device is configured to acquire a first image when an area of interest is illuminated with light of the first wavelength range of light and to acquire a second image when the area of interest is illuminated with light of the second wavelength range of light.

In some embodiments, the device is configured to store an acquired first image and an acquired second image. In some embodiments, the device is configured to store the third image.

In some embodiments, the device further comprises a display component configured to visually display a generated third image. In some embodiments, the device further comprises a display component configured to automatically visually display a generated third image. In some embodiments, the device further comprises a display component configured to visually display a generated third image upon receipt of command from a user.

In some embodiments, the device further comprises an illuminator configured to illuminate an area of interest with light comprising both the first wavelength range and the second wavelength range. In some embodiments, the illumination with the first wavelength range is simultaneous with illumination with the second wavelength range. In some embodiments, the illumination with the first wavelength range is separate from the illumination with the second wavelength range. In some embodiments, the light is incoherent light. In some embodiments, the illuminator is configured to illuminate the area of interest with white light. In some embodiments, the light source is configured to illuminate the surface of biological tissue with either light of the first wavelength range or light of the second wavelength range at any one time.

Figure 3:
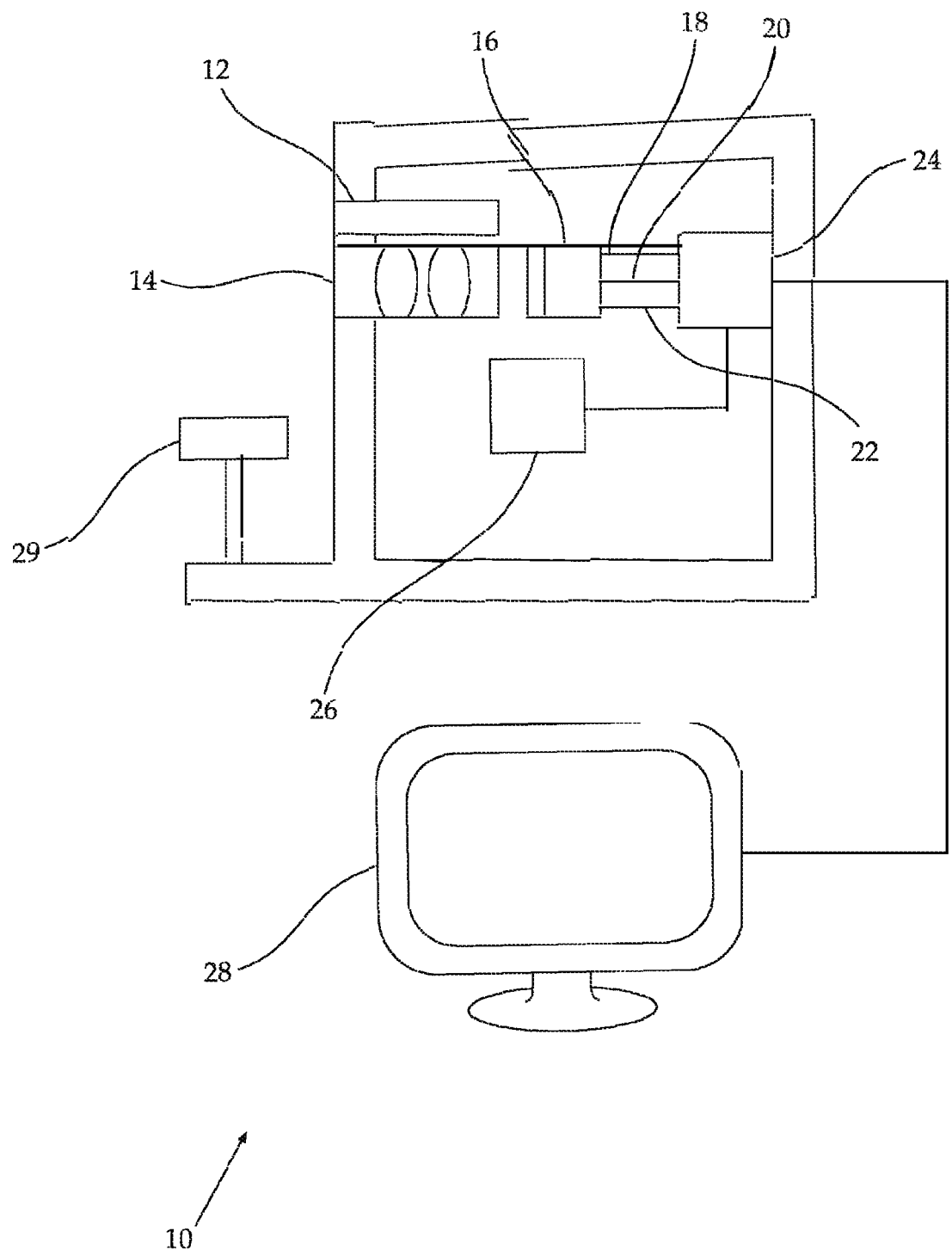
FIG. 3 is a schematic depiction of an embodiment of a fundus camera device as described herein suitable for implementing embodiments of the method described herein including a single RGB multicolor image-acquirer.

An embodiment of a device useful for generating an image of the surface of biological tissue, specifically a fundus camera 10 for generating an image of a retina, is schematically depicted in FIG. 3.

Device 10 is similar to known fundus cameras. Device 10 comprises an illuminator 12, configured to illuminate an area of interest of a retina with white incoherent light including substantially all wavelengths of light from 400 to 800 nm. Device 10 also comprises an objective 14, to gather light reflected from a retina and focus the light onto the light-detecting surface of a single multicolor image-acquirer 16, a 12-megapixel CMOS RGB detector array with a Bayer filter, having separate red pixels output 18, green pixels output 20 and blue pixel output 22. A processor 24 is configured to receive outputs 18, 20 and 22 and to generate a third image from the outputs in accordance with the teachings herein. Processor 24 is functionally associated with a memory 26 (an SDHC flash memory) to store acquired images and generated images. Processor 24 is also functionally associated with a display screen 28, a LED display screen.

For use, the chin of a subject is rested on chin-rest 29 so that the eye of a subject is appropriately positioned relative to objective 14. Illuminator 12, image-acquirer 16 and processor 24 are activated. Light from illuminator 12 is reflected from the area of interest of the retina and focused onto the light-detecting surface of image-acquirer 16 which simultaneously acquires data corresponding to three monochromatic images that are separately directed to processor 24: a red image through red pixel output 18, a green image through green pixel output 20 and a blue image through blue pixel output 22. Processor 24 stores the three acquired images in memory 26.

Depending on the user instructions (that can be changed through a device-user interface, not depicted), processor 24 generates an image from at least two of the acquired images, stores the generated image in memory 26 and automatically displays the generated image on display screen 28 in real time.

The user can instruct processor 26 to generate a third image as described above from:
- the green image as a first image and the red image as a second image;
- the blue image as a first image and the red image as a second image; or
- a combination (e.g., sum or weighted sum) of the blue and green images as a first image and the red image as a second image.

Image-acquirer 16 of device 10 is a CMOS (complementary metal oxide) RGB detector array with a Bayer filter, having separate red pixels output 18, green pixels output 20 and blue pixel output 22. In some related embodiments an image-acquirer is another detector technology, for example, a CCD (charge-coupled device) array, a PD (photodiode) array, or a LED (light-emitting diode) array. In some related embodiments, the image-acquirer is RGB but with a filter different from a Bayer filter (e.g., a filter similar to the filter used in a S9706 color sensor by Hamamatsu Photonics K.K. (Hamamatsu, Japan)) or a Foveon-X3 CMOS image-acquirer.

In some related embodiments, an image-acquirer has other colors. For example, in some embodiments the image-acquirer is an RGBE image-acquirer with four separate outputs: a red pixel output for acquiring a red image, a green pixel output for acquiring a green image, a blue pixel output for acquiring a blue image and an emerald pixel output for acquiring an emerald image. In some such embodiments, any of the green, blue and emerald images, singly or in combination of two or combination of three can be used a first image as described herein while the red image is used as a second image.

It is important to note that often the spectral response of a multicolor image-acquirer to a specific color is far from monochromatic. For example, the red of a typical Bayer filter has a peak sensitivity to light having wavelengths of 610 to 630 nm, that is gradually reduced towards 800 nm and is sharply reduced, but still significant down to 570 nm. Consequently, in some embodiments a second image such as a red image in the embodiment described above, includes wavelengths outside the range of 620 nm to 800 nm.

Figure 4:
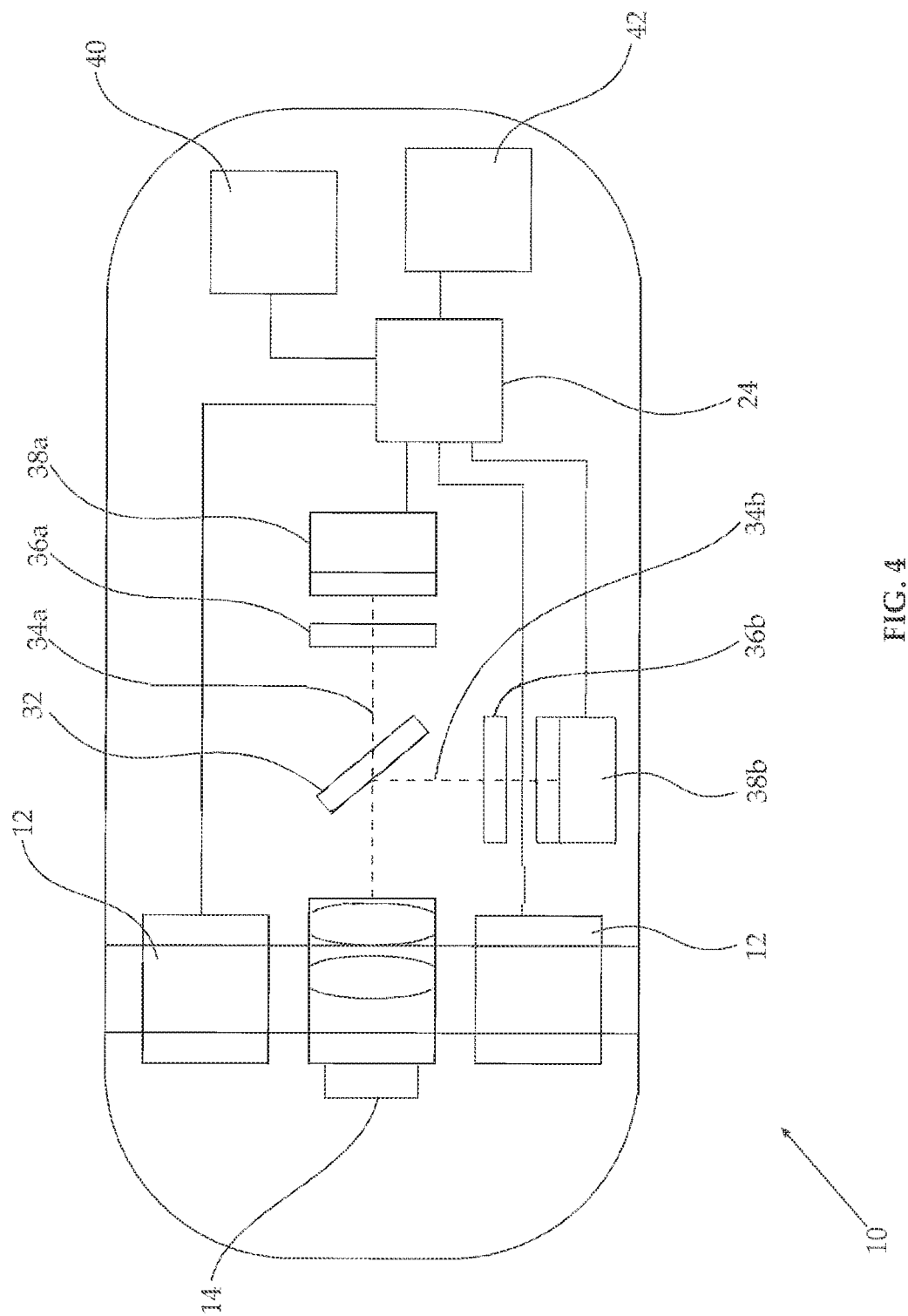
FIG. 4 is a schematic depiction of an embodiment of an ingestible gastrointestinal imaging device as described herein suitable for implementing embodiments of the method described herein including a beam-splitter, two wavelength filters and two monochromatic image-acquires.

An additional embodiment of a device useful for generating an image of the surface of biological tissue, specifically an ingestible device 30 for gastrointestinal imaging is schematically depicted in FIG. 4.

Device 30 is similar to known ingestible devices for gastrointestinal imaging such as the Pillcam™ (Given Imaging, Yokneam, Israel). Device 30 comprises an illuminator 12, configured to illuminate an area of interest of intestinal mucosa with white incoherent light including substantially all wavelengths of light from 400 to 800 nm. Device 30 also comprises an objective 14, to gather light reflected from the intestinal mucosa of a gastrointestinal tract in which device 30 is found and focus the light towards a beam-splitter 10 32, a half-silvered mirror, that directs light from objective 14 in two directions: in a first direction 34a through a first wavelength filter 36a (configured to pass light having a wavelength less than 620 nm and to block light having a wavelength greater than 620 nm) to impinge on the light-sensitive surface of a first image-acquirer 38a, a 12 megapixel monochrome CCD detector array and in a second direction 34b through a second wavelength filter 36b (configured to pass light having a wavelength greater than 620 nm and to block light having a wavelength less than 620 nm) to impinge on the light-sensitive surface of a second image-acquirer 38b, a 12 megapixel monochrome CCD detector array. Suitable wavelength filters are available, for example, from Lee Filters, Andover, Hampshire, England.

A processor 24 is configured to periodically receive acquired images from first image-acquirer 38a and second image-acquirer 38b, and to generate a third image from the images in accordance with the teachings herein. As known in the art of ingestible gastrointestinal imaging devices, processor 24 is functionally associated with a wireless Bluetooth® transmitter 40 that transmits acquired images and generated images to an external unit (not depicted). The various components of device 30 receive electrical power required for operation from power source 42, a lithium ion battery.

For use, device 30 is activated and ingested by a subject. Illuminator 12, image-acquirers 38a and 38b, processor 24 and transmitter 40 are activated. As device 30 1s propelled through the gastrointestinal tract of the subject, light from illuminator 12 is reflected from areas of interest of the intestinal mucosa retina and directed by objective 14 and beam-splitter 32 in first direction 34a and second direction 34b. Light traveling in first direction 34a passes through first wavelength filter 36a to the light sensitive surface of first image-acquirer 38a, that acquires a first image from the light. Light traveling in second direction 34b passes through second wavelength filter 36b to the light sensitive surface of second image-acquirer 38b, that acquires a second image from the light. Processor 24 receives the acquired first and second images from the respective image-acquirers 38 and generates a third image from the first and second images substantially as described above. Processor 24 then transmits the acquired images and the generated image to an external unit using transmitter 40.

In embodiments related to device 30, the device transmits acquired first images and second images to an external unit, and the external unit is configured to generate a third image from the acquired first and second images.

In some embodiments related to device 30, illuminator 12 comprises a white-light illumination source, such as a white-light emitting LED, to provide simultaneous illumination with light having wavelengths in both the first and second wavelength range.

In some embodiments related to device 30, illuminator 12 comprises at least two discrete light sources (e.g., colored-light emitting LEDs) to provide simultaneous illumination with light having wavelengths in both the first (e.g., 420 nm or 560 nm) and the second wavelength range (e.g., 620 nm).

Figure 5:
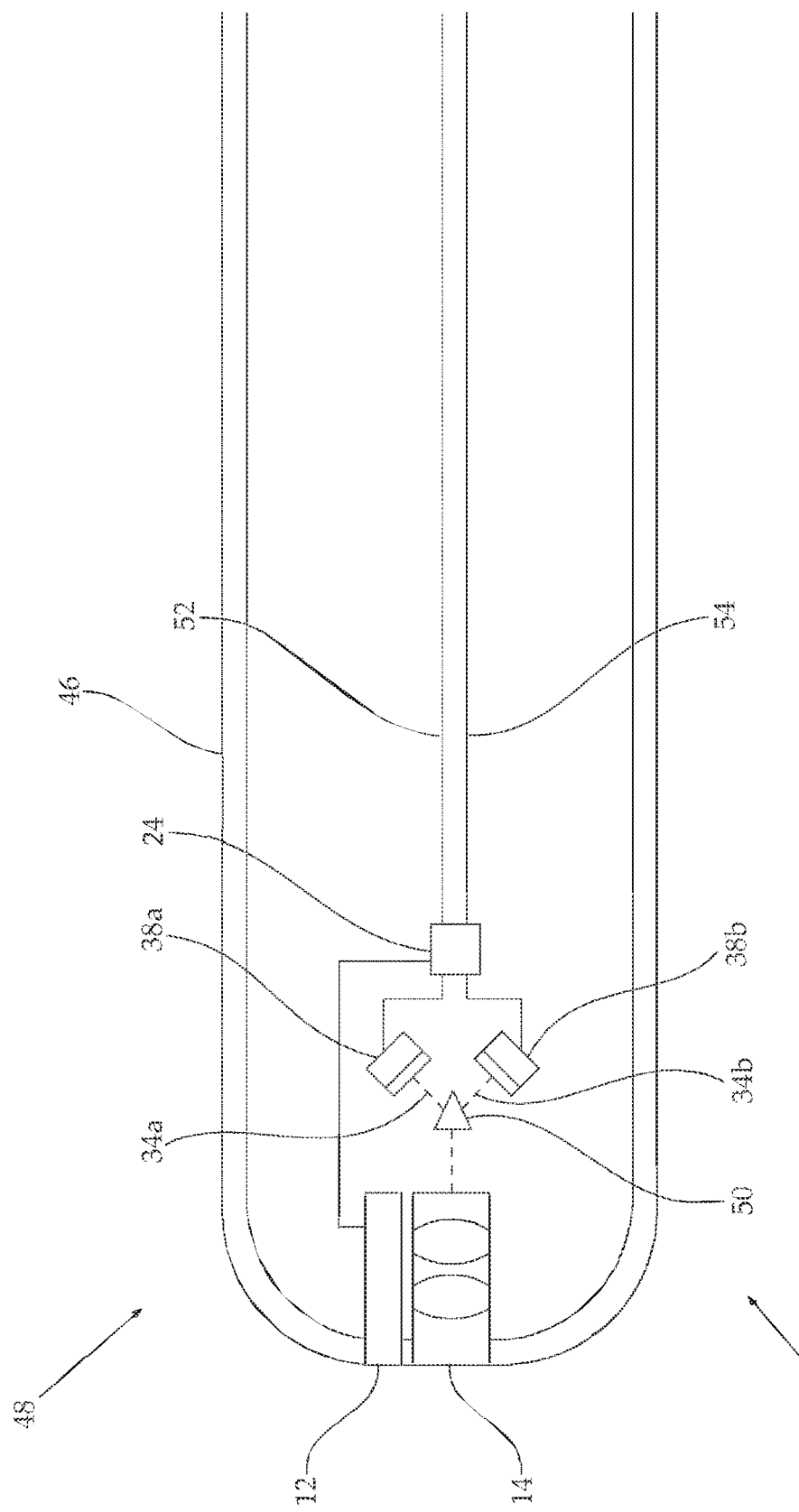
FIG. 5 is a schematic depiction of an embodiment of a flexible endoscope device as described herein suitable for implementing embodiments of the method described herein including a dichroic prism and two monochromatic image-acquirers.

An additional embodiment of a device useful for generating an image of the surface of biological tissue, specifically a flexible endoscope 44 for imaging the inner surfaces of bodily hollows is schematically depicted in FIG. 5. Device 44 comprises a flexible shaft 46 having a distal end 48 schematically depicted in detail in FIG. 5. Not depicted in FIG. 5 is the bulk of shaft 46, the proximal end of device 44, as well as other components such as steering components well known in the art of endoscopy.

Device 44 is similar to known flexible endoscopes. Device 44 comprises an illuminator 12, configured to illuminate an area of interest of a surface of a bodily hollow with white incoherent light including substantially all wavelengths of light from 400 to 800 nm. Device 44 also comprises an objective 14, to gather light reflected from the area of interest at which illuminator 12 is directed and focus the light towards a dichroic prism 50, that directs light from objective 14 in two directions: light having a wavelength of less than 600 nm is directed in a first direction 34a to impinge on the light-sensitive surface of a first image-acquirer 38a, a 12 megapixel monochrome CCD detector array while light having a wavelength of greater than 600 nm is directed in a second direction 34b to impinge on the light-sensitive surface of a second image-acquirer 38b, a 12 megapixel monochrome CCD detector array. Suitable dichroic prisms are available, for example, from Optec, Parabiago, Milano, Italy.

A processor 24 is configured to periodically receive acquired images from first image-acquirer 38a and second image-acquirer 38b, and to generate a third image from the images in accordance with the teachings herein. Processor 24 transmits acquired images for storage and generated images for storage and display to an external unit (not depicted) through communication cable 52 that passes through shaft 46 to the distal end of device 44. The various components of device 44 receive electrical power required for operation through lead 54.

For use, device 44 is activated and inserted into a hollow of a subject as known in the art. Illuminator 12, image-acquirers 38a and 38b and processor 24 are activated. As device 44 is steered inside the hollow, light from illuminator 12 is reflected from areas of interest of the inner surface of the hollow and directed by objective 14 and dichroic prism 50 in first direction 34a and second direction 34b. Light traveling in first direction 34a reaches the light sensitive surface of first image-acquirer 38a, that acquires a first image from the light. Light traveling in second direction 34b reaches the light sensitive surface of second image-acquirer 38b, that acquires a second image from the light. Processor 24 receives the acquired first and second images from the respective image-acquirers 38 and generates a third image from the first and second images substantially as described above. Processor 24 then transmits the acquired images and the generated image to an external unit through communication cable 52.

In embodiments related to device 30, the device transmits acquired first images and second images to an external unit, and the external unit is configured to generate a third image from the acquired first and second images. The generated image is displayed in real time, on a display device.

It is important to note that depending on the exact embodiment, device 44 is substantially any suitable type of flexible endoscope including, but not limited to, an esophagogastroduodenoscope, an enteroscope, a cholangiopancreatoscope, a colonoscope, a sigmoidoscope, a rhinoscope, a bronchoscope, a cystoscope, a gynoscope, a hysteroscope, a falloposcope, an amnioscope, a gastroscope, an otoscope, a laparoscope, a panendoscope or a fetoscope.

In device 44, the image-acquiring components are found at distal end 48 of device 44. In some embodiments, the image-acquiring components are found at the proximal end of the device and light from an area of interest on a surface of tissue is directed through a light guide (e.g., an optical fiber) passing from distal end 48 through flexible shaft 46 to the proximal end.

In a related non-depicted embodiment, a device as described herein includes a trichroic prism (or even an n-chroic prism, where n is greater than 3) instead of a dichroic prism to direct different wavelength ranges of light from objective 14 in different directions. At least two different wavelength ranges, in some embodiments more, are directed each to a different image-acquirer to acquire an image. A first image and a second image, as described hereinabove, are acquired and used to generate a third image in accordance with the teachings herein.

Figure 6:
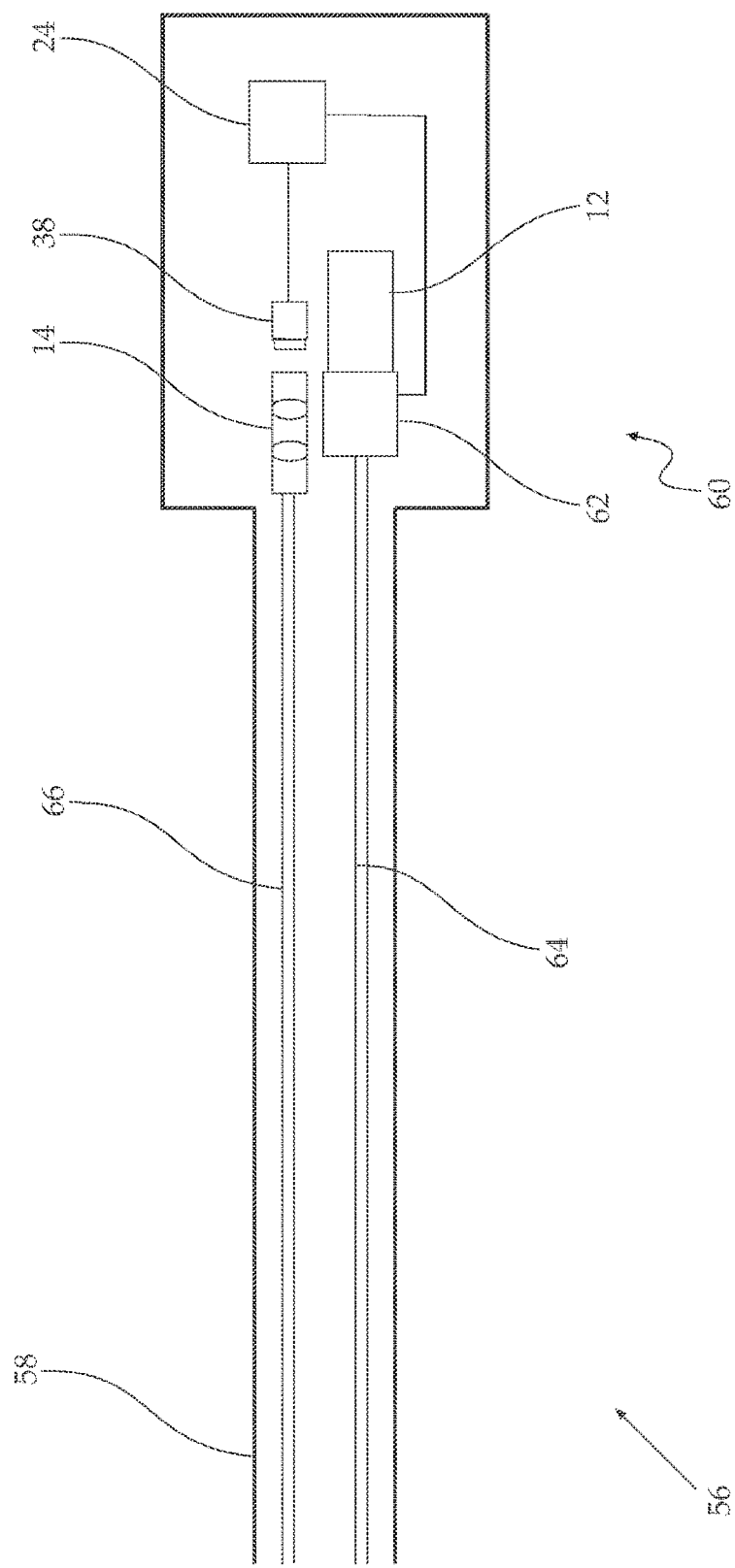
FIG. 6 is a schematic depiction of an embodiment of a rigid endoscope device as described herein suitable for implementing embodiments of the method described herein including two light sources and a single monochromatic image-acquirer.

An additional embodiment of a device useful for generating an image of the surface of biological tissue, specifically a rigid endoscope 56 (e.g., suitable for use as a laparoscope during keyhole surgery) for imaging the inner surfaces of bodily hollows is schematically depicted in FIG. 6. Device 56 comprises a rigid shaft 58 having a proximal end 60 schematically depicted in FIG. 6. Not depicted in FIG. 6 is the bulk of shaft 58, the distal end of device 56, as well as other components well known in the art of endoscopy.

Device 56 is similar to known rigid endoscopes. Device 56 comprises an illuminator 12. Illuminator 12 includes a white incoherent light source that is functionally associated with a changeable wavelength filter 62 having two states (determined, for example, by a rotating disk bearing two different wavelength filters). In a first state, light having a wavelength of less than 620 nm passes through changeable wavelength filter 62 into an illumination channel 64 that passes through shaft 58 to emerge through the distal tip of shaft 58 to illuminate an area of interest of a surface of bodily tissue, while light having a wavelength greater than 620 nm is blocked by changeable wavelength filter 62. In a second state, light having a wavelength of greater than 620 nm passes through changeable wavelength filter 62 into an illumination channel 64 that passes through shaft 58 to emerge through the distal tip of shaft 58 to illuminate an area of interest of a surface of bodily tissue, while light having a wavelength less than 620 nm is blocked by changeable wavelength filter 62. A processor 24 is configured to control the state of changeable wavelength filter 62.

Passing from the distal tip of shaft 58 is a light guide 66 (an optical fiber as known in the art of endoscopy) that directs light from the distal tip of shaft 58 to an objective 14. Objective 14 focuses light gathered from the distal tip of shaft 58 at the light-sensitive surface of an image-acquirer 38, a 12 megapixel multicolor (in some related embodiments, monochrome) CCD detector array.

Processor 24 is configured to repeatedly accept an image acquired by image-acquirer 38 when changeable wavelength filter 62 is in the first state as a first acquired image, then change the state of changeable wavelength filter 62 to the second state and accept an image acquired by image-acquirer 38 when changeable wavelength filter 62 is in the second state as a second acquired image. Thus, device 56 is configured to acquire the first image and the second image sequentially.

Using an algorithm based on standard stitching algorithms known in the art of digital photography, processor 24 is configured to identify corresponding pixels of an acquired first image and a succeeding or preceding acquired second image, and generate a third image from pairs of corresponding pixels from acquired first and second images in accordance with the teachings herein. Processor 24 transmits acquired images for storage and generated images for storage and display to an external unit (not depicted) through communication cable 52.

For use, device 56 is activated and inserted into a hollow of a subject as known in the art, e.g., through a surgical port. Illuminator 12, image-acquirer 38 and processor 24 are activated. The distal end of device 56 is directed at a surface so that light from illuminator 12 passes through illumination channel 64 towards an area of interest, and is reflected. Reflected light is directed through light guide 66 to objective 14. Objective 14 directs the light to the light sensitive surface of image-acquirer 38, that alternately acquires a first image and a second image depending on the state of changeable wavelength filter 62, as described above. Processor 24 receives the acquired first and second images from image-acquirer 38 and generates a third image from the first and second images substantially as described above. Processor 24 then transmits a generated image to be displayed on a display unit in real time.

Figure 7:
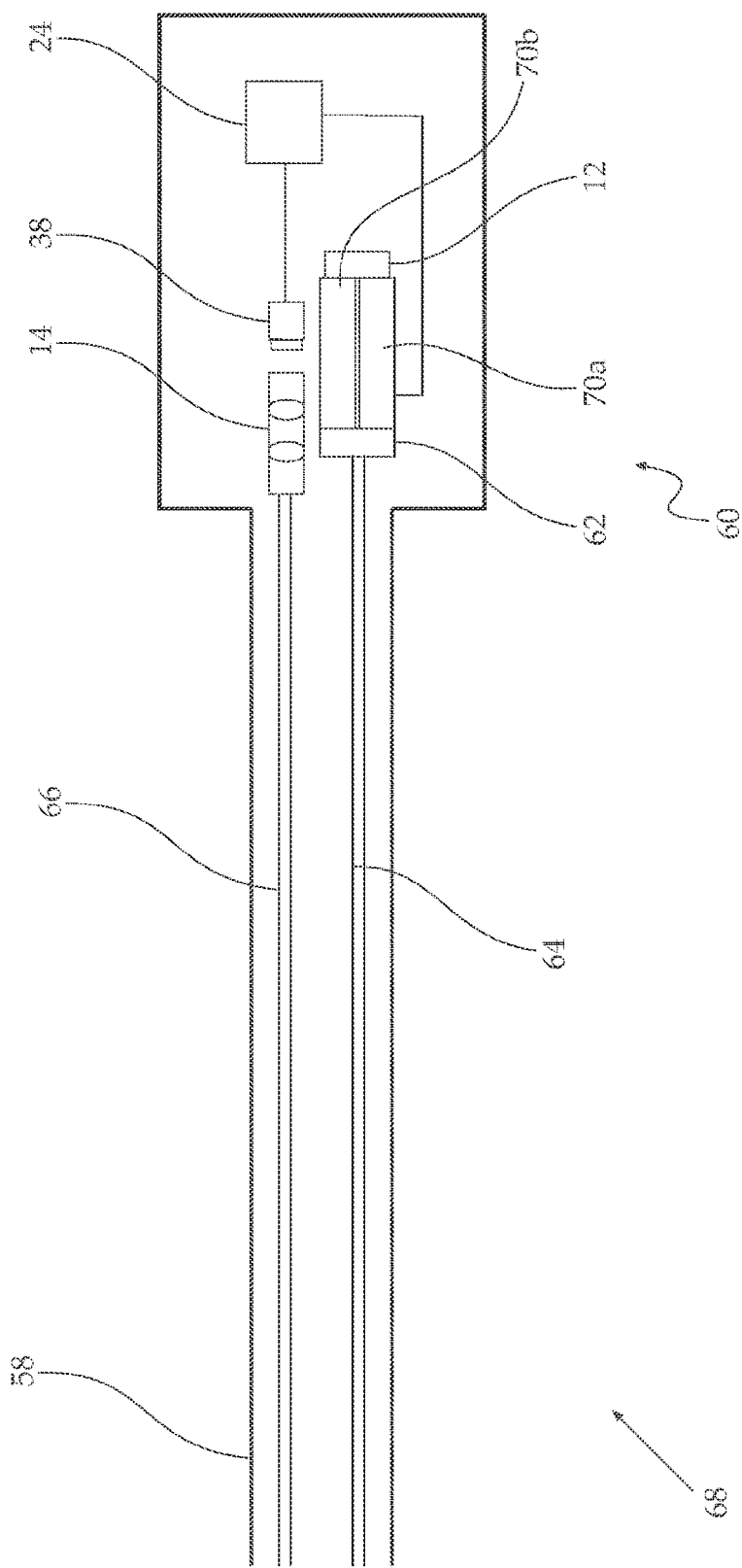
FIG. 7 is a schematic depiction of an embodiment of a rigid endoscope device as described herein suitable for implementing embodiments of the method described herein including two light sources and a single monochromatic image-acquirer.

In some embodiments described above, an illuminator configured to produce white light is used to illuminate an area of interest. In some alternate embodiments, a device includes an illuminator configured to produce a limited number of wavelengths of light to illuminate an area of interest. In such embodiments, at least one wavelength is between about 400 nm and about 620 nm (preferably between 475 nm and 560 nm where the difference in reflectance between blood and no blood is most pronounced) and at least one wavelength is between about 620 nm and about 800 nm (preferably between about 620 nm and 675 nm where the intensity of reflectance is highest). Typically, such an illuminator includes two separate light sources such as two monochromatic LEDs. An additional embodiment of a device useful for generating an image of the surface of biological tissue, specifically a rigid endoscope 68 (e.g., suitable for use as a laparoscope during keyhole surgery) for imaging the inner surfaces of bodily hollows is schematically depicted in FIG. 7.

Like device 56, device 68 is similar to known rigid endoscopes comprising a rigid shaft 58 having a proximal end 60. Device 68 comprises an illuminator 12 including two independently activatable substantially-monochromatic incoherent light sources, light-emitting diode 70a (green LED emitting light at 500 nm) and light-emitting diode 70b (red LED emitting light at 630 nm). When one or both LEDs 70a or 70b are activated, the emitted light passes into and through an illumination channel 64 that passes through shaft 58 to emerge through the distal tip of shaft 58 to illuminate an area of interest of a surface of bodily tissue.

Like in device 56, passing from the distal tip of shaft 58 is a light guide 66 that directs light from the distal tip of shaft 58 to an objective 14. Objective 14 focuses light gathered from the distal tip of shaft 58 at the light-sensitive surface of an image-acquirer 38, a 12 megapixel multicolor (in some related embodiments, monochrome) CCD detector array.

Processor 24 is configured to repeatedly activate LED 70a to illuminate an area of interest with monochromatic light having a wavelength of 500 nm and accept an image acquired by image-acquirer 38 as a first acquired image, and then to activate LED 70b to illuminate an area of interest with monochromatic light having a wavelength of 630 nm and accept an image acquired by image-acquirer 38 as a second acquired image. Thus, device 68 is configured to acquire the first image and the second image sequentially.

Like in device 56, processor 24 of device 68 is configured to identify corresponding pixels of an acquired first image and a succeeding or preceding acquired second image, and generate a third image from pairs of corresponding pixels from acquired first and second images in accordance with the teachings herein. Processor 24 transmits acquired images for storage and generated images for storage and display to an external unit (not depicted) through communication cable 52.

For use, device 68 is activated and inserted into a hollow of a subject as known in the art, e.g., through a surgical port. Illuminator 12, image-acquirer 38 and processor 24 are activated. The distal end of device 68 is directed at a surface so that light from illuminator 12 passes through illumination channel 64 towards an area of interest, and is reflected. Reflected light is directed through light guide 66 to objective 14. Objective 14 directs the light to the light sensitive surface of image-acquirer 38, that alternately acquires a first image and a second image depending on which LED 70a or 70b of illuminator 12 is activated, as described above. Processor 24 receives the acquired first and second images from image-acquirer 38 and generates a third image from the first and second images substantially as described above. Processor 24 then transmits a generated image to be displayed on a display unit in real time.

Depending on the exact embodiment, devices 56 and 68 are substantially any suitable type of rigid endoscope including, but not limited to, a laparoscope, an anoscope, a proctoscope, a rectoscope, an otoscope, a colposcope, an arthroscope, a thoracoscope, a sigmoidoscope, a rhinoscope, a bronchoscope, a cystoscope, a gynoscope, a gastroscope, a mediastinoscope, a panendoscope and a hysteroscope.

EXAMPLES

Example 1

A first laboratory mouse was anesthetized. The skin covering the abdominal cavity was cut to define a loose flap, and the flap secured with needles to a flat surface, skin side down.

Using an SD-300 spectral imaging camera (ASI, Migdal Haemek, Israel) fitted with a halogen lamp illuminator and a cross-polarizing filter set, a spectral image of a portion of the inner surface of the flap was acquired between 400 nm and 800 nm. The acquired image is reproduced, in black-and-white, in Figure IA. In Figure IB, the spectrum of a portion of the image where a blood vessel was present (portion a) and the spectrum of the image where no blood vessel was present (portion b) are displayed.

Example 2

A second laboratory mouse was anesthetized. The skin covering the abdominal cavity was cut to define a loose flap, and the flap secured with needles to a flat surface, skin side down.

Using an SD-300 spectral imaging camera (ASI, Migdal Haemek, Israel) fitted with a halogen lamp illuminator and a cross-polarizing filter set, a spectral image of a portion of the inner surface of the flap was acquired between 400 nm and 800 nm. An RGB image including all the image data acquired between 400 nm and 800 nm is reproduced in black-and-white in FIG. 2A.

A red-free narrow band (520 nm-580 nm) monochrome image using data acquired between is reproduced in black-and-white in FIG. 2B. Although the contrast is superior to the equivalent RGB image, the spatial resolution appears to be similar.

An image generated in accordance with an embodiment of the method described herein where the first wavelength range was 400 nm to 600 nm and the second wavelength range was 600 nm to 800 nm, and the mathematical formula describing the calculation of a pixel of the generated third image from the two corresponding pixels of the first and second images is: $P3(i)=[P1(i)/P2(i)]$. It is seen that the contrast and the spatial resolution of the generated image is significantly better than of both the RGB and the red-free image.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

For example, in some embodiments, any of the imaging assemblies described herein, such as the specific imaging assemblies described in detail with reference to a specific embodiments of the device: fundus camera 10, ingestible device 30, flexible endoscope 44, or a flexible endoscope 56 are used in other devices. For example, in some embodiments an imaging assembly such as described with reference to fundus camera 10 is used in an ingestible device, a flexible endoscope or a rigid endoscope (laparoscope).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Citation or identification of any reference in this application shall not be construed as an admission that such reference is available as prior art to the invention.

Section headings are used herein to ease understanding of the specification and should not be construed as necessarily limiting.

The invention claimed is:
1. A method for in vivo imaging of blood vessels, the method comprising:
   selecting a first wavelength range of light corresponding to a certain reflectance spectrum of a blood-containing region and higher absorbance in blood than non-blood bodily tissue;
   illuminating an area of interest of a surface with light comprising wavelengths within the first wavelength range, said first wavelength range including predominantly light having wavelengths of between 400 nm and 620 nm;
   acquiring a first pixelated image of light reflected from said area of interest of the surface at said first wavelength range of light;
   selecting a second wavelength range of light corresponding to a certain reflectance spectrum of a region devoid of blood and absorbance in blood similar to that of non-blood bodily tissue;
   illuminating said area of interest of the surface with light comprising wavelengths within the second wavelength range, said second wavelength range including predominantly light having wavelengths of between 620 nm and 800 nm; wherein said illuminating with light comprising wavelengths within said first wavelength range is performed simultaneously with said illuminating with light comprising wavelengths within said second wavelength range; wherein said illuminating is with light having at least two discrete wavelengths of light: at least one discrete wavelength within said first wavelength range and at least one discrete wavelength within said second wavelength range; wherein said illuminating comprises illuminating with incoherent light;
   directing light collected for acquiring said first image and said second image from said area of interest to a single image-acquirer;
   separating data acquired by said single image-acquirer constituting said first image from data acquired by said single image-acquirer constituting said second image;
   acquiring a second pixelated image of light reflected from said area of interest of the surface at said second wavelength range of light;
   generating by a processor a first image of an area of interest including at least one blood-containing feature of a surface of said first wavelength range corresponding to a certain reflectance spectra of a blood-containing region;
   generating by a processor a second image of an area of interest of a surface of a second wavelength range, being different from said first wavelength and corresponding to a certain reflectance spectra of a region devoid of blood; and generating by a processor a monochromatic image of at least one blood-containing feature by processing only said first image and said second image, by for each desired location i of said area of interest, identifying a corresponding pixel P1($i$) in said first image and a corresponding pixel P2($i$) in said second image; and calculating a pixel P3($i$) in said monochromatic image corresponding to said location i, by dividing pixels of the first and second images P1($i$) by P2($i$) or P2($i$) by P1($i$), wherein the monochromatic image has at least one of increased contrast between the blood-containing feature and adjacent tissue and increased spatial resolution at the border between the blood-containing feature and adjacent tissue as compared with the first and second images.

2. The method of claim 1, further comprising, displaying said monochromatic image.

3. The method of claim 1, comprising: directing light collected for acquiring said first image from said area of interest to a first image-acquirer to acquire said first image; and directing light collected for acquiring said second image from said area of interest to a second image-acquirer different from said first image-acquirer to acquire said second image.

4. The method of claim 1, wherein said first image and said second image are acquired sequentially.

5. A method for in vivo imaging of blood vessels, the method comprising:

selecting a first wavelength range of light corresponding to a certain reflectance spectrum of a blood-containing region and higher absorbance in blood than non-blood bodily tissue;

illuminating an area of interest of a surface with light comprising wavelengths within the first wavelength range, said first wavelength range including predominantly light having wavelengths of between 400 nm and 620 nm;

acquiring a first pixelated image of light reflected from said area of interest of the surface at said first wavelength range of light;

selecting a second wavelength range of light corresponding to a certain reflectance spectrum of a region devoid of blood and absorbance in blood similar to that of non-blood bodily tissue;

illuminating said area of interest of the surface with light comprising wavelengths within the second wavelength range, said second wavelength range including predominantly light having wavelengths of between 620 nm and 800 nm;

acquiring a second pixelated image of light reflected from said area of interest of the surface at said second wavelength range of light;

generating by a processor a first image of an area of interest including at least one blood-containing feature of a surface of said first wavelength range corresponding to a certain reflectance spectra of a blood-containing region;

generating by a processor a second image of an area of interest of a surface of a second wavelength range, being different from said first wavelength and corresponding to a certain reflectance spectra of a region devoid of blood; and generating by a processor a monochromatic image of at least one blood-containing feature by processing only said first image and said second image, by for each desired location i of said area of interest, identifying a corresponding pixel P1($i$) in said first image and a corresponding pixel P2($i$) in said second image; and calculating by a processor a pixel P3($i$) in said monochromatic image corresponding to said location i, by performing the following calculation $P3(i)=[(xP1(i)+m)^A/(yP2(i)+n)^B]$ and $P3(i)=[(yP2(i)+n)^B/(xP1(i)+m)^A]$, wherein A and B are, independently, any suitable positive number except 0 and including 1; wherein x and y are, independently, any suitable number including 1; and wherein m and n are, independently, any suitable number including 0, wherein the monochromatic image has at least one of increased contrast between the blood-containing feature and adjacent tissue and increased spatial resolution at the border between the blood-containing feature and adjacent tissue as compared with the first and second images.

6. The method of claim 5, wherein said illuminating with light comprising wavelengths within said first wavelength range is simultaneous with said illuminating with light comprising wavelengths within said second wavelength range.

7. The method of claim 5, wherein said illuminating is with light having at least two discrete wavelengths of light: at least one discrete wavelength within said first wavelength range and at least one discrete wavelength within said second wavelength range.

8. The method of claim 5, further comprising, displaying said monochromatic image.

9. The method of claim 5, wherein said illuminating comprises illuminating with incoherent light.

10. The method of claim 5, comprising: directing light collected for acquiring said first image from said area of interest to a first image-acquirer to acquire said first image; and directing light collected for acquiring said second image from said area of interest to a second image-acquirer different from said first image-acquirer to acquire said second image.

11. The method of claim 5, comprising: directing light collected for acquiring said first image and said second image from said area of interest to a single image-acquirer; separating data acquired by said single image-acquirer constituting said first image from data acquired by said single image-acquirer constituting said second image.

12. The method of claim 5, wherein said first image and said second image are acquired sequentially.

\* \* \* \* \*